United States Patent [19]

Behler et al.

[11] Patent Number: 5,312,932
[45] Date of Patent: May 17, 1994

[54] PROCESS FOR THE CONTINUOUS PRODUCTION OF PARTIAL GLYCERIDE SULFATES

[75] Inventors: Ansgar Behler, Bottrop; Uwe Ploog, Haan; Bernd Fabry, Korschenbroich; Frank Clasen, Hilden, all of Fed. Rep. of Germany

[73] Assignee: Henkel Kommanditgesellschaft auf Aktien, Duesseldorf, Fed. Rep. of Germany

[21] Appl. No.: 66,170

[22] PCT Filed: Nov. 25, 1991

[86] PCT No.: PCT/EP91/02208

§ 371 Date: Aug. 3, 1993

§ 102(e) Date: Aug. 3, 1993

[87] PCT Pub. No.: WO92/09569

PCT Pub. Date: Jun. 11, 1992

[30] Foreign Application Priority Data

Dec. 3, 1990 [DE] Fed. Rep. of Germany ....... 4038477

[51] Int. Cl.$^5$ .................................................. C11D 1/28
[52] U.S. Cl. ........................................ 554/90; 252/353
[58] Field of Search ............................ 554/90; 252/353

[56] References Cited

U.S. PATENT DOCUMENTS

| 2,285,773 | 6/1942 | Harris | 260/400 |
| 2,693,479 | 11/1954 | Ross | 260/400 |
| 2,979,521 | 4/1961 | Gray | 260/458 |
| 3,634,287 | 1/1972 | Woo | 252/353 |

FOREIGN PATENT DOCUMENTS

| 0267518 | 5/1988 | European Pat. Off. |
| 3821446 | 1/1989 | Fed. Rep. of Germany |
| 7570322 | of 0000 | Japan |
| 7877014 | of 0000 | Japan |

*Primary Examiner*—José G. Dees
*Assistant Examiner*—D. D. Carr
*Attorney, Agent, or Firm*—Ernest G. Szoke; Wayne C. Jaeschke; Henry E. Millson, Jr.

[57] ABSTRACT

Process for the continuous production of partial glyceride sulfates comprising the steps of A. continuously reacting partial glycerides with gaseous sulfur trioxide, B. subjecting the resulting acidic sulfonation products to ageing, and C. neutralizilng the aged acidic sulfonation products with an aqueous base in the presence of a buffer.

20 Claims, No Drawings

PROCESS FOR THE CONTINUOUS PRODUCTION OF PARTIAL GLYCERIDE SULFATES

This invention relates to a process for the continuous production of partial glyceride sulfates by reaction of partial glycerides with gaseous sulfur trioxide and subsequent neutralization of the reaction products with aqueous bases.

Sulfated partial glycerides, particularly monoglyceride sulfates are anionic surfactants which are distinguished by high foaming power, good cleaning performance and excellent dermatological compatibility (*Anionic Surfactants, Pt. I, Surfactant Science Series*, Vol. 7, W. M. Linfield (Ed.), Marcel Dekker Inc., New York 1976, page 219).

Monoglyceride sulfates are normally produced from glycerol which is first reacted with oleum (U.S. Pat. No. 2,693,479) or chlorosulfonic acid (JP 78/77014) to form the glycerol sulfate which is then transesterified in the presence of a triglyceride to form the monoglyceride sulfate (Lipidos 26, 19 (1966)). In addition, German application DE-A-38 21 446 discloses a process for the production of monoglyceride sulfates by reaction of glycerol with chlorosulfonic acid in an organic solvent, in which fatty acids or fatty acid esters are used for the transesterification. However, the sulfonation with oleum or chlorosulfonic acid leads to products of high electrolyte content and is therefore not advantageous.

It is known from Philipp. J. Sci. 311 (1965) that mixtures of triglycerides and glycerol can be transesterified in the presence of alkaline catalysts. It is also proposed in this document that the glycerol fatty acid partial esters obtained be sulfated with sulfuric acid or oleum.

The sulfation of glycerol with sulfur trioxide and the subsequent transesterification of the glycerol sulfate formed with triglycerides is known from U.S. Pat. No. 2,979,521. However, products having unsatisfactory degrees of sulfonation are obtained in this way.

The direct reaction of monoglycerides with sulfur trioxide in liquid su)fur dioxide (U.S. Pat. No. 3,634,287) or with oleum as the sulfonating agent (JP 50/70322) is also known. In addition, European patent application EP-A-0 267 518 discloses the reaction of partial glycerides with sulfur trioxide in nitrogen-containing solvents. The use of solvents is also a disadvantage for the industrial production of such partial glyceride sulfates because they cannot be left in the product, but instead have to be removed after the reaction in a very energy-and time-consuming step.

Accordingly, the problem addressed by the present invention was to provide a process for the production of partial glyceride sulfates which would be free from the disadvantages mentioned above.

The present invention relates to a process for the continuous production of partial glyceride sulfates, characterized in that technical partial glycerides are continuously reacted with gaseous sulfur trioxide, the acidic sulfonation products are subjected to ageing and are then neutralized with aqueous bases in the presence of a buffer.

The invention is based on the observation that partial glyceride sulfates having particularly high degrees of sulfonation are obtained by ageing the crude sulfonation products and using a buffer in the neutralization step.

Partial glycerides are known chemical substances which may be obtained by the relevant methods of organic preparative chemistry, for example by transesterification of triglycerides With glycerol. Monofatty acid and difatty acid glycerol esters and technical mixtures thereof based on aliphatic carboxylic acids containing 6 to 22 carbon atoms and 0, 1, 2 or 3 double bonds are suitable for the production of the partial glyceride sulfates. More specifically, the monoglycerides and diglycerides of caproic acid, caprylic acid, capric acid, lauric acid, myristic acid, palmitic acid, palmitoleic acid, stearic acid, oleic acid, elaidic acid, petroselic acid, linoleic acid, linolenic acid, arachic acid, gadoleic acid, behenic acid or erucic acid may be used. It is preferred to use lauric acid monoglyceride and/or diglyceride.

As usual in oleochemistry, the fatty acid components of the partial glycerides may also be technical mixtures such as are formed, for example, in the pressure hydrolysis of natural fats and oils, such as for example coconut oil, palm oil, palm kernel oil, rapeseed oil, sunflower oil, coriander oil or beef tallow. Hydrogenated coconut oil fatty acid monoglyceride and/or diglyceride is/are preferably used. Small quantities of triglycerides or free glycerol, which may be present as impurities in the technical partial glyceride mixtures, do not affect the sulfation reaction.

The sulfonation of the fatty acid glycerol esters with gaseous sulfur trioxide may be carried out by the known method for fatty acid lower alkyl esters (J. Falbe (ed.), "Surfactants in Consumer Products", Springer verlag, Berlin-Heidelberg, 1987, page 61), preferably using reactors operating on the falling-film principle. The sulfur trioxide is diluted with an inert gas, preferably air or nitrogen, and used in the form of a gas mixture which contains the sulfonating agent in a concentration of 1 to 8% by volume and, more particularly, 2 to 5% by volume.

The sulfonation may be carried out with 0.95 to 1.8 mol gaseous sulfur trioxide per mol of the hydroxyl groups present in the partial ester mixtures. To obtain high degrees of sulfonation and light-colored products, it has proved to be optimal to carry out the sulfonation with 1 to 1.3 mol sulfur trioxide per mol hydroxyl groups in the partial glyceride ester.

The sulfonation may be carried out at temperatures of 70° to 98° C. To produce products having a high degree of sulfonation, it has proved to be optimal to select a temperature of 90° to 95° C.

After sulfonation, the crude sulfonation product is subjected to ageing. This step may be carried out continuously, for example in a tube coil, or discontinuously, for example in a tank reactor. The ageing step may be carried out over a period of 1 to 240 minutes and preferably over a period of 5 to 30 minutes at temperatures of 70° to 98° C. and preferably at temperatures of 90° to 95° C. If ageing is carried out at low temperatures within the limits indicated, long residence times are necessary to obtain high degrees of sulfonation and vice versa.

After ageing, the acidic sulfonation products formed during the sulfonation reaction are stirred together with aqueous bases into an aqueous buffer solution and neutralized, a pH value of 5.5 to 9 and preferably 6.5 to 8 having to be maintained because otherwise the ester bond would be hydrolyzed or the sulfate group would be eliminated. Suitable buffers are, for example, 1 to 5% by weight aqueous solutions of sodium triphosphate, sodium hydrogen carbonate or citric acid.

Suitable bases for the neutralization step are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and also primary, secondary or tertiary $C_{1-4}$ alkyl amines. The neutralization bases are preferably used in the form of 5 to 55% by weight aqueous solutions, 5 to 25% by weight aqueous sodium hydroxide solutions being preferred.

The sulfonation products are complex mixtures of which more than 50% by weight contain sulfation products of the primary and secondary hydroxyl groups of the partial glycerides, i.e. monoglyceride and diglyceride sulfates. In addition, the reaction mixture may contain open-chain and cyclic glycerol sulfates and also alpha-glycerol ester sulfonates, products containing sulfate and sulfonate groups, soaps, sulfonated soaps and glycerol. Where unsaturated partial glycerides are used as starting materials, an addition of the sulfur trioxide onto the double bond of the fatty acid component also takes place to a minor extent with formation of internal glycerol ester sulfonates.

After neutralization, the sulfonation products may be bleached in known manner by addition of hydrogen peroxide or sodium hypochlorite solution. Based on the solids content of the solution of sulfonation products, 0.2 to 2% by weight hydrogen peroxide, expressed as 100% substance, or corresponding quantities of sodium hypochlorite are used. In addition, it is advisable to add a preservative, for example formaldehyde solution, p-hydroxybenzoate, sorbic acid or any other known preservative, for stabilization against bacterial contamination.

The partial glyceride sulfates have surface-active properties and are suitable for the production of powder-form or liquid detergents and cleaning products and also hair-care and personal hygiene products.

The following Examples are intended to illustrate the invention without limiting it in any way.

EXAMPLES

Starting materials:

a) Lauric acid monoglyceride
Monomuls ® 90-L-16, Chemische Fabrik Grünau GmbH, Illertissen
Composition: 68% by weight $C_{12}$ monoglyceride
32% by weight $C_{12}$ diglyceride
Average molecular weight: 136
Hydroxyl value: 413 b) Coconut oil fatty acid monoglyceride
Composition: 46% by weight $C_{12/14}$ monoglyceride
32% by weight $C_{12/14}$ diglyceride
7% by weight $C_{12/14}$ triglyceride
10% by weight glycerol
Average molecular weight: 140
Hydroxyl value: 401

EXAMPLE 1

Sulfonation of lauric acid monoglyceride.

In a continuously operating falling-film reactor (length 120 cm, cross-section 1 cm, educt throughput 600 g/h) with jacket cooling and a side inlet for gaseous $SO_3$, 1650 g (5 mol) of the technical monoglyceride A were reacted with sulfur trioxide at 95° C. The ratio used was 1.3 mol $SO_3$ per mol hydroxyl groups in the partial ester. The sulfur trioxide was driven out by heating from a corresponding quantity of 65% by weight oleum, diluted with nitrogen to a concentration of 5% by volume and contacted with the monoglyceride film via a nozzle. The crude sulfonation product was subjected to ageing and, to this end, was stored for 30 minutes at 90° C. It was then stirred together with 37% by weight sodium hydroxide solution into a 1% by weight solution of sodium triphosphate and neutralized at pH=6.5 to 8. The characteristic data of the reaction product are set out in Table 1.

COMPARISON EXAMPLE 1

The procedure was as in Example 1, except that the ageing step after sulfonation and before neutralization was omitted. The characteristic data of the reaction product are set out in Table 1.

EXAMPLE 2

1980 g (5 mol) of a technical coconut oil fatty acid monoglyceride B were reacted with sulfur trioxide as in Example 1. The ratio used was again 1.3 mol sulfur trioxide per mol hydroxyl groups in the partial ester. A product having the characteristic data shown in Table 1 was obtained after ageing and neutralization.

COMPARISON EXAMPLE 2

The procedure was as in Example 2, except that the ageing step after sulfonation and before neutralization was omitted. The characteristic data of the reaction product are set out in Table 1.

The anionic surfactant content (WAS) and the unsulfonated components (US)—in the present case the total of free partial glyceride and soap—were determined in accordance With DGF-Einheitsmethoden, Stuttgart, 1950–1984, H-III-10 and G-II-6b. The sulfate content was expressed as sodium sulfate, the soap content was determined by thin layer chromatography and the water content was determined by the Fischer method.

The degree of sulfonation S° was determined in accordance with the following formulae:

$$x = \frac{M^{Ed} WAS}{M^{Pr}} \text{ and } S° = \frac{x \cdot 100}{x + US}$$

where $M^{Ed}$ and $M^{Pr}$ stand for the molecular weights of the starting materials and the sulfonated products, respectively.

TABLE I:

Characteristic Data of the Sulfonation Products

Percentages as % by Weight

TABLE I

| Ex. | Characteristic data of the sulfonation products Percentages as % by weight | | | | | |
|---|---|---|---|---|---|---|
| | WAS % | PG % | Soap % | $SO_4^{2-}$ % | $H_2O$ % | S° % |
| 1 | 15.1 | 2.5 | 0.3 | 5.5 | 76.6 | 80 |
| 2 | 16.5 | 1.4 | 0.4 | 6.2 | 75.5 | 86 |
| C1 | 13.4 | 3.2 | 0.3 | 6.4 | 76.7 | 75 |
| C2 | 14.0 | 2.7 | 0.3 | 7.2 | 75.7 | 79 |

Legend: PG = Content of unsulfonated partial gyceride

We claim:

1. A process for the continuous production of partial glyceride sulfates comprising the steps of A) reacting at least one partial glyceride with gaseous sulfur trioxide to produce at least one acidic sulfation product;

B) ageing the at least one acidic sulfation product; and

C) neutralizing the aged acidic sulfation product with aqueous base in the presence of a buffer.

2. The process of claim 1 wherein in step A) the at least one partial glyceride is a technical mixture of partial glycerides.

3. The process of claim 1 wherein step A) is carried out in a continuously operating falling-film reactor.

4. The process of claim 1 wherein step A) is carried out at a temperature in the range of from 70° to 98° C.

5. The process of claim 4 wherein said temperature is in the range of 90° to 95° C.

6. The process of claim 1 wherein step A) is carried out using a ratio of from 0.95 to 1.8 mols of sulfur trioxide per mol of hydroxy groups in the at least one partial glyceride.

7. The process of claim 6 wherein said ratio is from 1 to 1.3.

8. The process of claim 1 wherein step B) is carried out over a period of from 1 to 240 minutes.

9. The process of claim 8 wherein said period is from 5 to 30 minutes.

10. The process of claim 1 wherein step B) is carried out at a temperature in the range of from 70° to 98° C.

11. The process of claim 10 wherein said temperature is in the range of from 90° to 95° C.

12. The process of claim 1 wherein step C) is carried out with from 5 to 55% by weight aqueous base selected from the group consisting of alkali metal hydroxides, alkaline earth metal oxides and hydroxides, ammonia, mono-, di- and tri-$C_{2-4}$ alkanolamines and primary, secondary and tertiary $C_{1-4}$ alkyl amines.

13. The process of claim 12 wherein step C) is carried out with from 5 to 25% by weight of aqueous base.

14. The process of claim 9 wherein step C) is carried out at a pH in the range of from 5.5 to 9.

15. The process of claim 14 wherein said pH is in the range of from 6.5 to 8.

16. The process of claim 1 wherein in step A) the at least one partial glyceride is a technical mixture of partial glycerides, step A) is carried out at a temperature in the range of from 70° to 98° C., step A) is carried out using a ratio of from 0.95 to 1.8 mols of sulfur trioxide per mol of hydroxy groups in the at least one partial glyceride; and step B) is carried out over a period of from 1 to 240 minutes, and at a temperature in the range of from 70° to 98° C.

17. The process of claim 16 wherein step A) and B) are both carried out at a temperature in the range of from 90° to 95° C.; in step A) said ratio is from 1 to 1.3; and step B is carried out over a period of from 5 to 30 minutes.

18. The process of claim 16 wherein step A) is carried out in a continuously operating falling-film reactor.

19. The process of claim 16 wherein step C) is carried out at a pH in the range of from 5.5 to 9.

20. The process of claim 25 wherein step C) is carried out at a pH in the range of from 6.5 to 8.

* * * * *

UNITED STATES PATENT AND TRADEMARK OFFICE
CERTIFICATE OF CORRECTION

PATENT NO. : 5,312,932
DATED : May 17, 1994
INVENTOR(S) : Behler, et. al.

It is certified that error appears in the above-indentified patent and that said Letters Patent is hereby corrected as shown below:

In claim 14, column 6, line 7, "claim 9", should read:
-- claim 1 --.

In claim 20, column 6, line 30, "claim 25", should read:
-- claim 17 --.

Signed and Sealed this

Eleventh Day of April, 1995

Attest:

BRUCE LEHMAN

*Attesting Officer*                *Commissioner of Patents and Trademarks*